United States Patent [19]
Witherby et al.

[11] Patent Number: 5,571,012
[45] Date of Patent: Nov. 5, 1996

[54] DISPOSABLE PROPHY ANGLE AND ADAPTER

[75] Inventors: Kenneth Witherby, Loveland; Sheryl L. Wittstruck, Fort Collins, both of Colo.

[73] Assignee: Teledyne Industries, Inc., Los Angeles, Calif.

[21] Appl. No.: 371,101

[22] Filed: Jan. 11, 1995

[51] Int. Cl.$^6$ ........................................ A61C 3/06
[52] U.S. Cl. .................... 433/125; 433/126; 433/133
[58] Field of Search ............................. 433/125, 126, 433/128, 132, 133

[56] References Cited

U.S. PATENT DOCUMENTS

| | | |
|---|---|---|
| 3,163,934 | 1/1965 | Wiseman . |
| 3,740,853 | 6/1973 | Brahler . |
| 3,798,777 | 3/1974 | Reiter . |
| 3,869,877 | 3/1975 | Brahler . |
| 4,182,041 | 1/1980 | Girard ............... 433/115 |
| 4,310,310 | 1/1982 | Bailey ............... 433/126 |
| 5,028,233 | 7/1991 | Witherby ........... 433/125 |
| 5,040,978 | 8/1991 | Falcon et al. ..... 433/126 |
| 5,121,220 | 6/1992 | Butler ................ 433/126 |
| 5,156,547 | 10/1992 | Bailey ............... 433/126 |
| 5,178,538 | 1/1993 | Eckert ............... 433/125 |
| 5,219,285 | 6/1993 | Meller et al. ..... 433/126 |
| 5,224,859 | 7/1993 | Kraenzle ........... 433/126 |
| 5,334,020 | 8/1994 | Eckert ............... 433/125 |

FOREIGN PATENT DOCUMENTS

| | | |
|---|---|---|
| 508696 | 10/1929 | Germany . |
| 876737 | 4/1953 | Germany . |

Primary Examiner—Cary E. O'Connor
Attorney, Agent, or Firm—Lockwood, Alex, Fitzgibbon & Cummings

[57] ABSTRACT

Disposable prophy angles for use in combination with a reusable metal adapter on a contra-angle dental hand piece. The disposable prophy angles are assembled from three mass-produced components formed from plastic or other inexpensive material. Each disposable prophy angle is formed from a main body part having a nose portion and a barrel portion, a nose cap portion which with the nose portion forms an enclosed nose portion housing and an integral rotary part disposed in the enclosed nose portion housing which has a driven power input gear, bearing formations and a protruding prophy cup receiving button. Each reusable metal adapter has a shaft with gears mounted on opposite ends. One end of the adapter is inserted in the barrel portion with the gear on the inserted end in driving engagement with driven power input gear. The gear on the opposite end of the adapter is connected to the power output of a contra-angle dental hand piece.

3 Claims, 2 Drawing Sheets

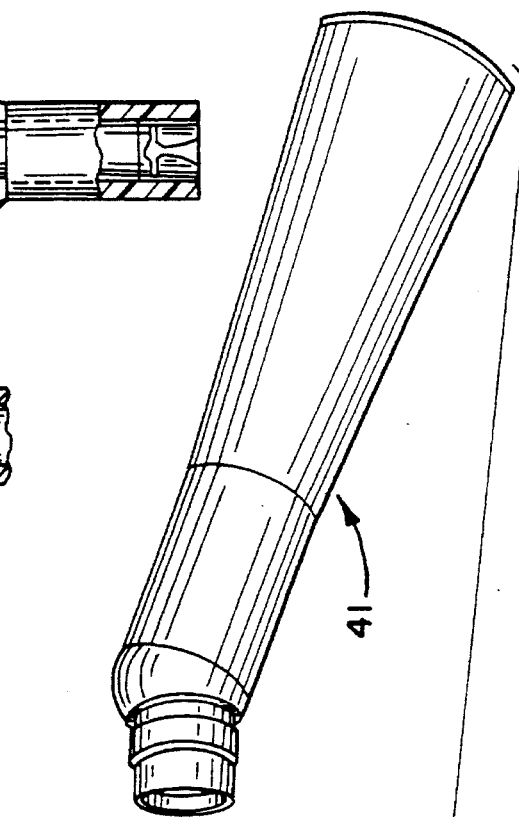

5,571,012

DISPOSABLE PROPHY ANGLE AND ADAPTER

BACKGROUND AND DESCRIPTION OF THE INVENTION

This invention relates, generally, to new and useful innovations and improvements in disposable prophy angles adapted to be used on contra-angle dental hand pieces. More particularly, the invention relates to disposable prophy angles consisting of three component parts which can be economically mass produced and readily assembled into completed units. The prophy angles are "disposable" in the sense that they are sufficiently inexpensive so as to be discardable after one use. The component parts may, for example, be injection molded from suitable plastics, die cast from aluminum or otherwise formed. The invention also relates to a power transmitting adapter whereby the disposable prophy angles can be driven from a contra-angle dental hand piece.

Heretofore, two general types of prophy angles (i.e. dental prophylaxis right angle hand pieces) have been available. One type has been the relatively expensive permanent type formed of metal parts suitable for repeated usage and requiring sterilization before each use. The other general type of prophy angle is the disposable type which are usually formed of plastics and which are disposable after one-time use. One such disposable prophy angle is disclosed U.S. Pat. No. 5,028,233 dated Jul. 2, 1991.

The disposable prophy angles of the present invention are used in association with a power transmitting adapter having one end inserted in the barrel or tubular socket of a disposable prophy angle while the other end is operatively coupled with the power output end of a contra-angle dental hand piece of known type. The present invention also includes a preferred form of the power transmitting adapter.

An important object of the invention is the provision of a reusable metal adapter for use in combination with disposable prophy angles which allows the disposable prophy angles to be used on contra angle dental hand pieces. The metal adapter being reusable and providing the input power to the disposable prophy angles, thereby increases the durability and reliability of the combination while reducing the number of component parts of the prophy angles and in turn reduces the cost of the latter.

A further object of the invention is the provision of a new and improved disposable prophy angle formed of only three component parts (not counting the conventional prophy cup) with each component part being integrally formed of plastic or other inexpensive material such as die cast aluminum and readily assemblable with the other two parts on a production basis into permanently assembled units which are inexpensive, reliable, rugged and durable for one-time use and which are energy efficient in receiving, transmitting and delivering power from the input side to the output side so as to drive the prophy cups.

A further object of the invention is the provision of a reusable power transmitting adapter one end of which is insertable in the barrel portion of a disposable prophy angle of the present invention and the opposite end of which is connected in driving relationship with the output end of a contra-angle dental hand piece.

Certain other objects of the invention will be apparent to those skilled in the art in the light of the foregoing and the following detailed description of a preferred embodiment of the invention taken in connection with the accompanying drawings, wherein:

BRIEF DESCRIPTION OF THE DRAWINGS

FIG. 1 is an exploded perspective view of a disposable prophy angle embodying the present invention;

FIG. 2 is an exploded perspective view of a prophy angle of the present invention in association with a power transmitting adapter and the power delivering end of a contra-angle dental hand piece;

FIG. 4 is a top plan view of the main body part of the prophy angle shown in FIG. 1;

FIG. 5 is a side elevational view taken on lines 5—5 of FIG. 4;

FIG. 6 is an end elevational view taken on lines 6—6 of FIG. 5;

FIG. 7 is a fragmentary sectional view taken on lines 7—7 of FIG. 6;

FIG. 8 is a bottom plan view, partly broken away and partly in section, of the main body part of the prophy angle of FIG. 1;

In FIGS. 1–3, the prophy angle of the present invention is indicated generally at 5 and consists of a main body part indicated generally at 6, a nose cap part indicated generally at 7 and an integral output gear part indicated generally at 8. A conventional prophy cup indicated generally at 10 and formed of a resilient rubber-like material is detachably mounted on a button 11 on one end of the output gear part 8.

Figure 3:
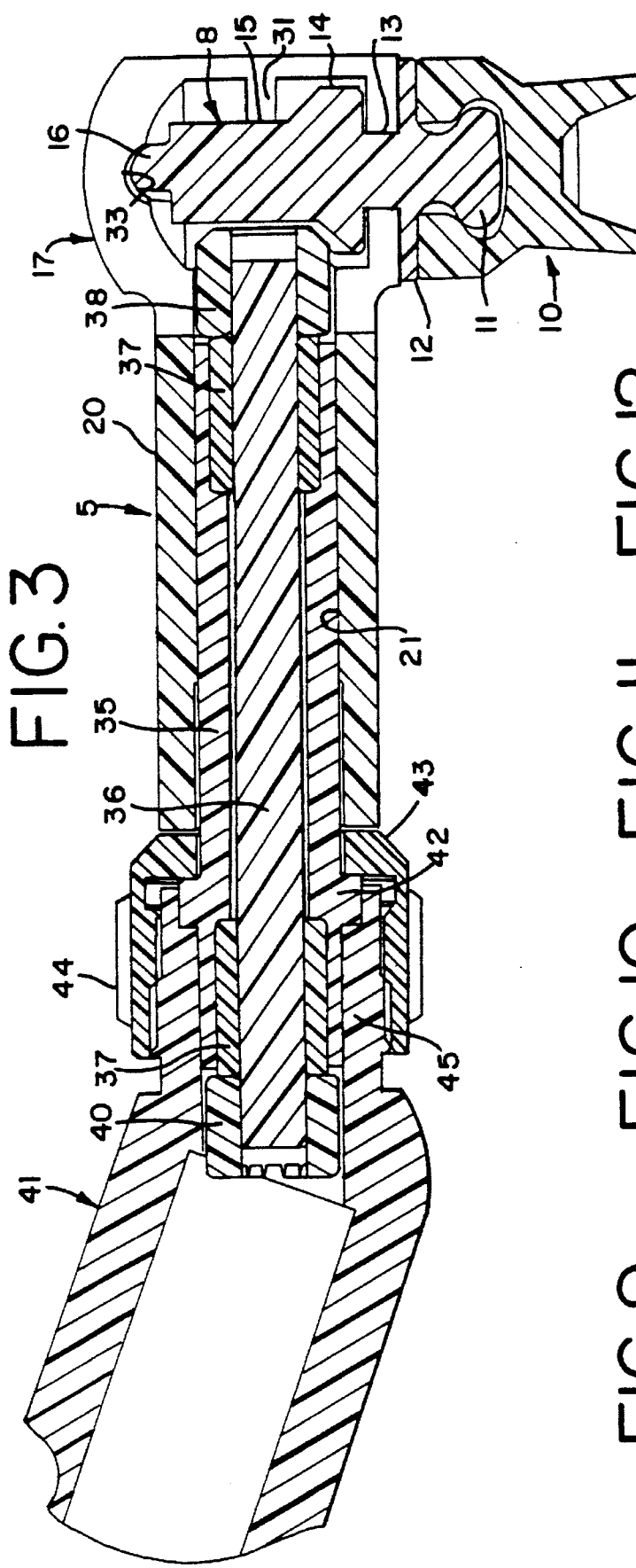
FIG. 3 is a longitudinal sectional view showing the disposable prophy angle of FIGS. 1 and 2 in assembled relationship with the power transmitting adapter of FIG. 2 which in turn is shown assembled to the power output end of the contra-angle of FIG. 2.

Referring to the integral output gear part 8 as being vertically oriented as shown in FIG. 3, the prophy cup receiving button 11 is on the bottom end of the part 8 as viewed in FIG. 3 and above which slinger ring 12 is located. Next above the slinger ring 12 is a cylindrical bearing section 13, and above that a level output gear 14. Proceeding upward, there is an upper cylindrical bearing section 15 above the gear 14. At its upper end the output gear part 8 may have a hemi-spherical thrust bearing section 16.

The body of the output gear part 8 above the slinger ring 12 is encased within the nose portion indicated generally at 17 (FIGS. 2 and 3) of the housing of the prophy angle 5. The nose portion 17 is formed by the nose forming cap part 7 and the mating nose forming portion 18 of the main body part 6.

In addition to the nose forming portion 18, the main body part 6 includes a barrel or tubular portion 20 which has a longitudinal internal bore 21 which receives one end 22 (FIG. 2) of a power transmitting adapter indicated generally at 23. Adjacent its outer end the barrel 20 is provided with a tapered entry slot 24 for releasably receiving a locking pin 25 (FIG. 2) on the adapter 23. On its underside as shown in FIG. 1, and also as shown in FIGS. 5–8, the nose forming portion 18 has a planar surface 26 which mates with the planar surface 27 of the nose cap part 7.

Figure 12:
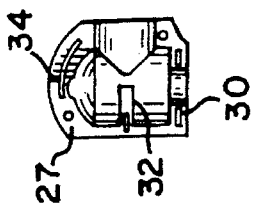
FIG. 12 is a plan view of the inner bonding surface of the nose cap which mates with the nose portion of the main body portion.
Figure 11:
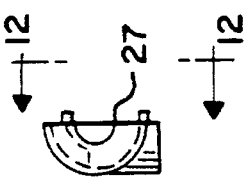
FIG. 11 is an end elevational view taken on lines 11—11 of FIG. 9.
Figure 10:
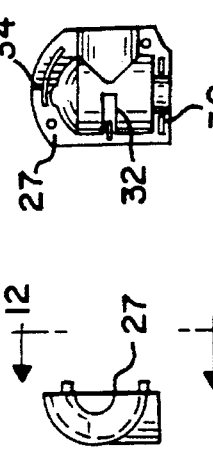
FIG. 10 is a sectional view taken on lines 10—10 of FIG. 9.
Figure 9:
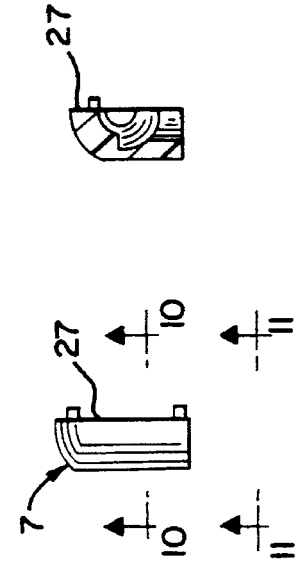
FIG. 9 is a side elevational view of the nose cap part of the prophy angle of FIG. 1 and taken on lines 9—9 of FIG. 1.

The lower cylindrical bearing section 13 on the output gear part 8 is journaled for rotation in a bearing formed by the mating together of the semicircular formation 28 (FIG. 8) on the nose forming portion 18 and the semicircular formation 30 (FIGS. 1 and 12) on the nose cap part 7. One side of the upper bearing section 15 is journaled for rotation in a semicircular bearing formation formed in part by the mating together of the bearing formation 31 (FIG. 8) on the interior of the nose forming portion 18 and the bearing formation 32 formed on the interior of the nose cap 7. The hemi-spherical upper end of the thrust bearing section 16 of the output gear part 8 rotates in a correspondingly hemi-spherical bearing surface 33 (FIG. 8) in the inner upper interior of the nose forming portion 18 and the mating hemi-spherical bearing surface 34 (FIGS. 1 and 2) of the nose cap 7.

Referring to FIGS. 2 and 3, the power transmitting adapter 23 comprises an outer housing or sheath 35 in which rotates a drive shaft 36. The drive shaft 36 is journaled adjacent its opposite ends in bushings 37—37. Gears 38 and 40 are mounted on opposite ends of the drive shaft 36. The bevel gear 38 drivingly meshes and engages with the bevel gear 14 on the output gear part 8. The gear 40 is driven by a drive shaft (not shown) forming part of a contra-angle dental hand piece of known type indicated generally at 41. For example, the contra-angle dental hand piece 41 may be a Kavo CDPA assembly.

The housing 35 has a shoulder 42 (FIG. 3) which is engaged by the shoulder 43 on a coupling nut 44 which screws onto a nose 45 on the contra-angle hand piece 41 as shown in FIG. 3 thereby operatively connecting the drive shaft 36 and the gears 38 and 40 in driven relationship with the contra-angle 41.

It will apparent from FIG. 3 that as the drive shaft 36 is driven by the contra-angle hand piece 41 the gear 38 rotates therewith and in turn, drives the gear part 8. As the button 11 on the output gear part 8 rotates, it carries with it the prophy cup 10.

The three component parts of the disposable prophy angle 5 may be formed from suitable plastic or other materials which have adequate strength and durability for their respective intended functions. By way of example only, the main housing part 20 and the nose cap 7 may be formed from a suitable grade of nylon (e.g. Nylon 6). The gear-part 8 may be formed from nylon or acetal resin (e.g. Nylon 6/6—10% glass filled or Acetal Resin—10% glass filled). These plastics are suitably inexpensive and are economically producible in production quantities and the respective parts may be injection molded therefrom. Alternatively, one or more of these three component parts can be die cast or otherwise formed from aluminum or other materials by suitable known procedures.

After the component parts have been assembled the assembly can be made permanent by bonding the mating surfaces of the main housing part 20 and the nose cap 7. The bonding may be obtained by use of suitable adhesives, sonic welding in the case of plastics or other known techniques.

What is claimed is:

1. A disposable prophy angle permanently assembled from component parts consisting of an integral vertically oriented output gear part, an integral main body part and an integral nose cap part, said main body part and nose cap part being secured together on common mating surfaces thereof after insertion therebetween of said output gear part, and said disposable prophy angle being drivable by the power input gear on one end of a power transmitting adapter removably inserted into said main body part, the other end of said adapter being operatively connectable to a contra angle dental hand piece;

said output gear part having a protruding prophy cup receiving button on its bottom end, a laterally extending slinger ring above said button, a lower rotary bearing section above said slinger ring, a driven gear above said lower rotary bearing member, and an upper rotary bearing section above said driven gear;

said main body part comprising a horizontal longitudinally extending barrel portion and a nose forming portion on one end matable with said nose cap part; and said nose cap part when mated with said nose forming portion on said common mating surfaces forming together therewith an enclosed nose portion of said disposable prophy angle which houses all of said output gear part above said slinger ring and also said power input gear on said inserted end of a power transmitting adapter, and said enclosed nose portion providing internal stationary bearing formations in which said lower rotary bearing section and said upper rotary bearing section are journaled for rotation, said common mating surfaces being co-planar with a plane longitudinally bisecting said barrel portion of said main body part.

2. The disposable prophy angle of claim 1 wherein said output gear part has a rotary thrust bearing on its upper end and said enclosed nose portion provides an internal stationary bearing formation in which said rotary thrust bearing rotates.

3. The disposable prophy angle of claim 1 wherein said nose cap part and said nose forming portion of said main body part form left and right hand halves of said enclosed nose portion and mate together at said common mating surfaces.

* * * * *